United States Patent [19]

Suh et al.

[11] Patent Number: 5,015,663

[45] Date of Patent: May 14, 1991

[54] TREATMENT OF CONDITIONS REQUIRING ENHANCED OXYGEN AVAILABILITY OF MAMMALIAN TISSUES

[75] Inventors: John T. Suh, Maple Glen; Robert G. Pendleton, Hatfield; Charles E. Pendley, II, Abington; Kin T. Yu, Collegeville; Paul R. Menard, North Wales; Alain B. Schreiber, Fort Washington, all of Pa.

[73] Assignee: Rhone-Poulenc Rorer Pharmaceuticals Inc., Fort Washington, Pa.

[21] Appl. No.: 488,190

[22] Filed: Mar. 5, 1990

Related U.S. Application Data

[62] Division of Ser. No. 333,520, May 11, 1989, Pat. No. 4,948,582, which is a division of Ser. No. 211,486, Jun. 23, 1988, Pat. No. 4,861,795.

[51] Int. Cl.$^5$ .............. A61K 31/21; A61K 31/19; A61K 31/40; A61K 31/55

[52] U.S. Cl. ............... 514/510; 514/569; 514/408; 514/422; 514/212; 424/529; 424/533

[58] Field of Search .............. 514/510, 512, 408, 422, 514/212

[56] References Cited

U.S. PATENT DOCUMENTS 4,861,795  8/1989  Suh et al. .............. 514/510
4,948,582  8/1990  Suh et al. .............. 424/529

Primary Examiner—Stanley J. Friedman
Assistant Examiner—Terry Wilson
Attorney, Agent, or Firm—Imre Balogh; James A. Nicholson

[57] ABSTRACT

Disclosed are pharmaceutical compositions containing naphthoic acid derivatives and method of use for enhancing oxygen availability to mammailian tissue.

8 Claims, No Drawings

TREATMENT OF CONDITIONS REQUIRING ENHANCED OXYGEN AVAILABILITY OF MAMMALIAN TISSUES

This application is a division of co-pending application Ser. No. 333,520, filed on May 11, 1989, which in turn, is a division of application Ser. No. 211,486 issued as U.S. Pat. No. 4,861,795.

BACKGROUND OF THE INVENTION

1. Field of the Invention

This invention relates to a method of enhancing oxygen availability to mammalian, especially human, tissue. More particularly, the invention relates to modifying the affinity of hemoglobin for oxygen and thereby effecting adequate supply of oxygen to human tissue necessary for metabolism.

Certain clinical conditions are associated with increased demand for oxygen, namely, respiratory distress syndrome, shock, low cardiac output, heart and lung diseases, anemia, hyperthyroidism, cirrhosis of the liver, exercise, high altitude climbing and the like. Under these conditions it is desirable, and sometimes of life-saving necessity, to effect higher oxygen availability to the patient than is normally available. The present invention addresses methods and compositions to that end.

Blood circulating through the heart, arteries, veins and capillaries is vital to the functioning of the body, inter alia, for carrying nutriment and oxygen to the body cells and carbon dioxide back through the systemic veins for gas-exchange in the lungs. Blood consists of plasma containing the red blood corpuscles or erythrocytes, the white blood corpuscles or leukocytes, and blood platelets or thrombocytes. The oxygen transport system in man is the erythrocyte which contains the iron-protein conjugate, called hemoglobin. While the supply of oxygen to the cell is influenced by many factors, such as, the content and partial pressure of oxygen in the inhaled air, cardiac output and blood volume, the passive diffusion of oxygen from the lungs and its release to the tissues is mainly controlled by the affinity of hemoglobin for oxygen.

This affinity is expressed by an oxygen hemoglobin dissociation curve having oxygen tension denoted by mm Hg, and oxygen saturation denoted by percentage as the coordinates. At 50% oxygen saturation ($P_{50}$) the oxygen tension is 27 mm Hg. An increase in blood acidity, carbon dioxide content, ionic concentration or temperature is known to shift the oxygen-hemoglobin equilibrium curve to the right by reducing hemoglobin affinity for oxygen and thereby increasing oxygen availability to the tissues. On the other hand, an increase in alkalinity of blood and tissues as well as a decrease in body temperature is known to shift the equilibrium curve to the left, and therefore, decrease oxygen availability.

Affinity of hemoglobin for oxygen is regulated by the level of certain intracellular organic phosphates, notably, 2,3-diphosphoglyceric acid (hereinafter 2,3-DPG). Thus, the equilibrium curve can be shifted from normal either to the left or to the right by changing the concentration of intracellular 2,3-DPG in the red blood cells. The synthesis of 2,3-DPG is catalyzed by the enzyme 2,3-diphosphoglycerate synthase, the stimulation of which results in the maintenance or accumulation of 2,3-DPG in red blood cells. The degradation of 2,3-DPG, on the other hand, is catalyzed by the enzyme 2,3-diphosphoglycerate phosphatase. The inhibition of this enzyme, similarly, would result in the maintenance and accumulation of 2,3-DPG in red blood cells, accompanied by the maintenance and increase of oxygen availability.

2. Description of the Prior Art

It has been recognized by the prior art that oxygen-hemoglobin affinity is mainly regulated by the level of 2,3-DPG in mammalian red blood cells. (See for example: Benesh et al., Intracellular organic phosphates as regulators of oxygen release by hemoglobin, Nature, London, 221: 6/8-622, 1969; Oski et al. The Interrelationship Between Red Blood Cell Metabolites, Hemaglobin, and the Oxygen-Equilibrium Curve, Progress in Hemotology 7: 33, 1971.) Clinical conditions associated with alterations of 2,3-DPG levels include adaptation to high altitude, anemia, cirrhosis of the liver, heart and lung diseases and hyperthyroidism. These relationships were investigated by, for example:

Keys et al., Respiratory properties of the arterial blood in normal man and with patients with disease of the liver. Position of the oxygen dissociation curve, J. Clin. Invest., 17:59, 1938;

Morse et al., The position of the oxygen dissociation curve of the blood in cyanotic congenital heart disease, J. Clin. Invest., 29:1098, 1950;

Edwards et al., Improved oxygen release: An adaptation of mature red cells to hypoxia, J. Clin. Invest. 47:1851–1857, 1968;

Gahlenbeck et al., Veraenderung der Saurstoff-bindungskurven des Blutes by Hyperthyreosen und nach Gabe von Trijodthyronin bei Gesunden und bei Ratten. Klin. Wschr. 46:547, 1968;

Keys et al., The position of the oxygen dissociation curve of human blood at high altitude, Amer. J. Physiol 115:292, 1936. Under these conditions delivery of oxygen to the tissues is impaired and the body's natural responses are inadequate to correct the tissue hypoxia.

To relieve hypoxic conditions, pharmaceutically active compounds, which shift the oxygen-hemoglobin dissociation curve to the right, were proposed and shown to be effective using appropriate test procedures. (See U.S. Pat. No. 4,626,431, U.S. Pat. No. 4,626,432 and EPO 0 093 381.) In addition to in vivo application, the compounds were also proposed for use in vitro blood storage to prolong useful shelf-life thereof. As to the mechanism or pathway involved in accomplishing the desired result, the compounds are said to induce right-displacement of the oxygen-dissociation curve.

The prior art has also discovered that the synthesis and degradation of 2,3-DPG are catalyzed by two enzymatic activities known respectively as 2,3-diphosphoglycerate synthase and 2,3-diphosphoglycerate phosphatase. (See: Rose, Z. B., J. Biol. Chem. 243, 4810, 1968 and Rose et al., J. Biol. Chem. 245, 3232, 1970.) Accordingly, the stimulation of 2,3-diphosphoglycerate synthase or the inhibition of 2,3- diphosophoglycerate phosphatase, or both, shall result in the maintenance or increase of 2,3-DPG levels in the red blood cells.

The present invention is drawn to the inhibition of 2,3-diphosphoglycerate phosphatase by the utilization of certain compounds found to be effective to accomplish said inhibition and thereby providing for the maintenance and/or accumulation of 2,3-DPG levels which, as shown by the prior art, control the dissociation of oxygen/ hemoglobin. The mechanism involved in the inhibition of 2,3-diphosphoglycerate phosphatase is believed to be as follows.

2,3-diphosphoglycerate phosphatase is activated by a number of cellular metabolites, such as 2-phosphoglycolate, chloride and phosphate ions. 2-Phosphoglycolate is by far the most potent activator enhancing the activity of 2,3-diphosphoglycerate phosphatase by about 1600 fold at optimal concentrations. Preventing or lowering the interaction of 2-phosphoglycolate with 2,3-diphosphoglycerate phosphatase affords an excellent mechanism to control the 2,3-DPG levels in the cells allowing utilization of inhibitors in low concentrations.

SUMMARY OF THE INVENTION

The present invention relates to naphthoic acid derivatives of formula I:

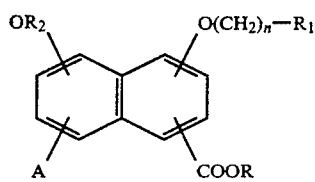

wherein
R is H, alkyl, aryl or aminoalkyl;
$R_1$ is H, alkyl, amino, $NR_3R_4$ where $R_3$ and $R_4$ is H or alkyl, or $R_3$ and $R_4$ can form a cyclic amino group with N to which they are attached;
$R_2$ is H, acyl, aminoacyl, alkyl, substituted alkyl wherein the substituents are aryl, azacycloalkyl, CONHR aryloxy, or alkoxyalkyl;
A is H, halo, $CF_3$, OH or

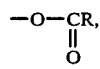

aminoalkyl, aryl, acyl, alkoxy, or alkoxyalkyloxy; and n is 0-6; and
pharmaceutically acceptable salts thereof. These compounds have been heretofore known for their hypotensive activity. (U.S. Pat. No. 3,673,238 relates to such compounds and the same is incorporated herein by reference.)

In the above-denoted formula the various groups have the meanings that follow.

The alkyl group means alkyl having up to 8 carbon atoms and include straight-chained and branched groups, including methyl, ethyl, propyl, isopropyl, butyl, isobutyl, tert-butyl, amyl, iso-amyl, heptyl, hexyl and the like. By halo is meant chloro, bromo, iodo, and fluoro.

Amino means amino or an amino derivative such as $-NH_2$, $-NH-C(NH_2)=NH$ when in formula I n is 2-6 or

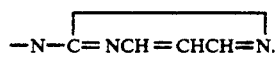

The cyclic amino ring formed by $R_3$ and $R_4$ and the N atom to which they are attached contains 3 to 8 atoms.

The cycloalkyl group contains 3 to 10 carbon atoms; and the aryl group contains up to 12 carbon atoms. The preferred cycloalkyl groups include cyclopropyl, cyclobutyl, cyclopentyl, cyclohexyl, cyclopentyl, adamantyl or norbornyl. The preferred groups in aryl are phenyl and naphthyl.

Particularly preferred compounds are:

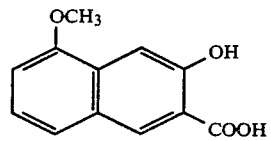
(a) 5-methoxy-3-hydroxy-2-naphthoic acid

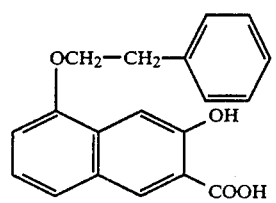
(b) 5-phenetoxy-3-hydroxy-2-naphthoic acid

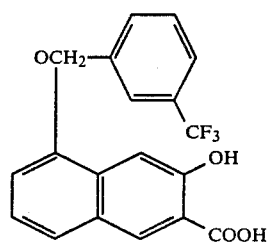
(c) 5-(3-trifluoromethylbenzyloxy)-3-hydroxy-2-naphthoic acid

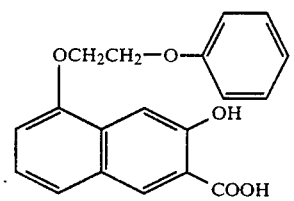
(d) 5-phenoxyethoxy-3-hydroxy-2-naphthoic acid

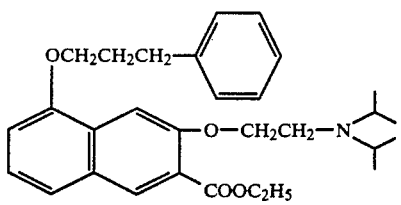
(e) ethyl 5-(3-phenylpropoxy)-3-(2-diisopropylamino-ethoxy)-2-naphthoate (f) ethyl 5-(3,4-dichlorobenzyloxy)-3-hydroxy-2-naphthoate

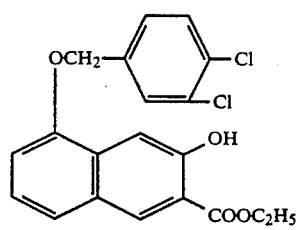
(g) 5-acetoxy-3-hydroxy-2-naphthoic acid

-continued

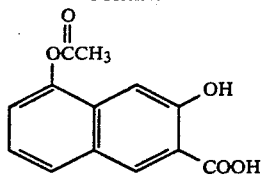

(h) 5-benzyloxy-3-hydroxy-2-naphthoic acid

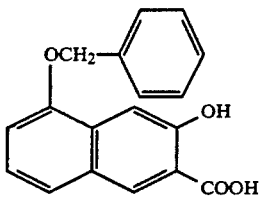

(i) ethyl 5-(3-phenylpropoxy)-3-(2-piperidino-ethoxy)-2-naphthoate

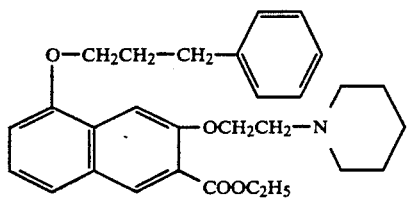

(j) ethyl 5-cyclohexylmethoxy-3-(2-(1-azacyclo-heptyl)-ethoxy)-2-naphthoate

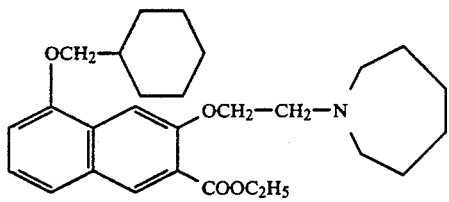

(k) ethyl 5-cyclohexylmethoxy-3-diisopropyl-aminoethoxy-2-naphthoate

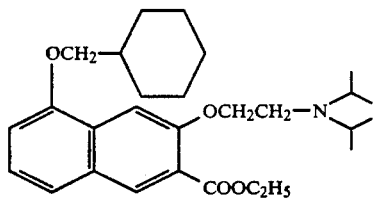

(l) ethyl 5-(4-chlorobenzyloxy)-3-diisopropyl-ethoxy-2-naphthoate

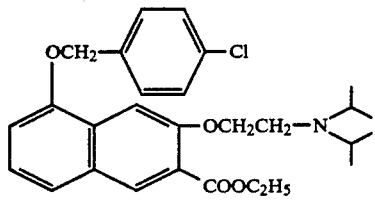

(m) ethyl 5-benzyloxy-3-(3-dimethylamino)-propoxy-2-naphthoate

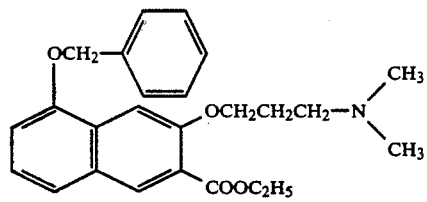

-continued (o) 5-(4-fluorobenzyloxy)-3-acetoxy-2-naphthoic acid

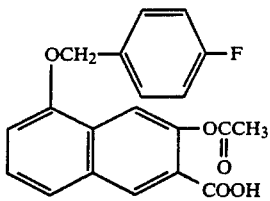

(p) ethyl 3,5-bis[2-(1-pyrrolidinyl)ethoxy]-2-naphthoate monohydrochloride

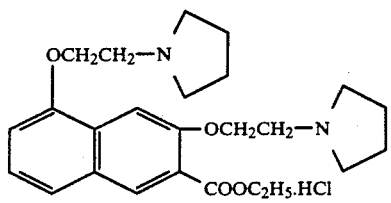

(q) 5-(3,4-dichlorobenzyloxy)-3-hydroxy-2-naphthoic acid

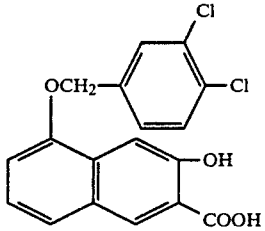

(r) 3-hydroxy-5-(3-phenylpropoxy)-2-naphthoic acid

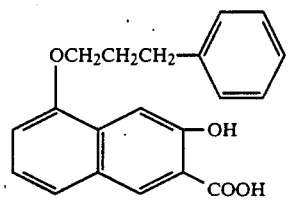

(s) 5-(2,4-dichlorobenzyloxy)-3-hydroxy-2-naphthoic acid

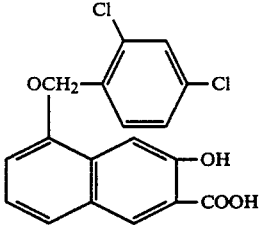

(t) 5-(2,6-dichlorobenzyloxy)-3-hydroxy-2-naphthoic acid

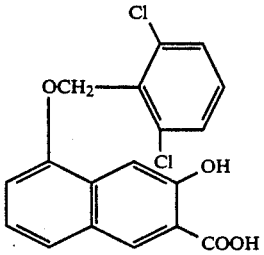

(u) 5-[3-(3,4-dichlorophenyl)-propoxy]-3-hydroxy-2-naphthoic acid

-continued

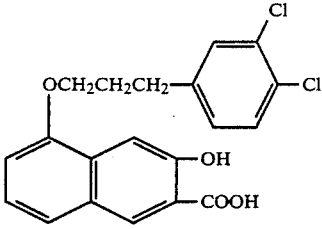

(v) 5-(4-fluorobenzyloxy)-3-hydroxy-2-naphthoic acid

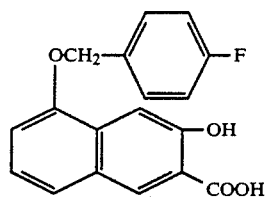

(w) 3,5-bis-(3,4-dichlorobenzyloxy)-2-naphthoic acid

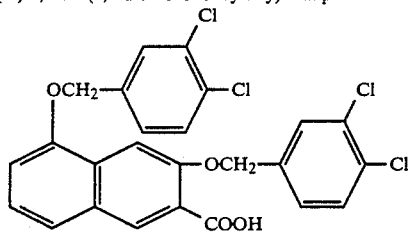

(x) 3-hydroxy-5(undecenyloxy)-2-naphthoic acid

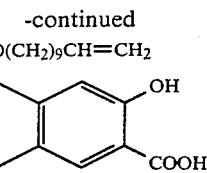

(y) 5-benzyloxy-3-dichloroacetoxy-2-naphthoic acid

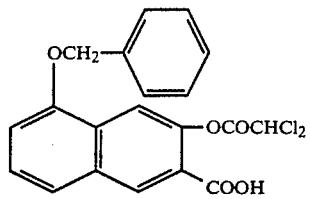

The pharmaceutically acceptable, non-toxic salts include salts of inorganic acids such as hydrochloric, hydrobromic, sulfuric and phosphoric, and of organic acids such as acetic, propionic, glycolic, lectic, malonic, succinic, malic, fumaric, tartaric, citric, ascorbic, benzoic, hydroxybenzoic, aminosalicylic, cinnamic, mandelic, benzenesulfonic, toluenesulfonic, nicotinic, isonicotinic, and the like.

DETAILED DESCRIPTION OF THE INVENTION

The compounds of the present invention may be prepared by art-recognized methods from available starting materials, may also be prepared by the general procedure described in U.S. Pat. No. 3,673,238, or may be obtained from chemical supply houses, such as Aldrich Chem. Co.

The following synthetic schemes may be used to advantage in obtaining compounds used in the present invention.

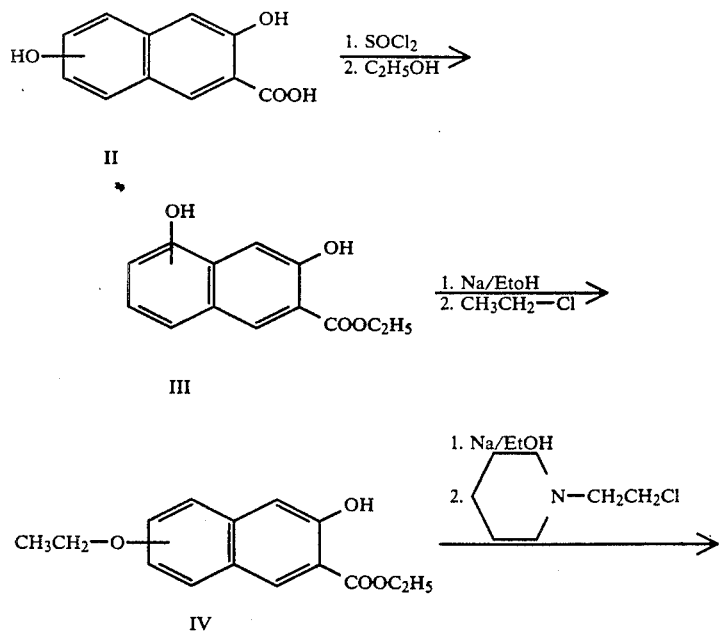

-continued

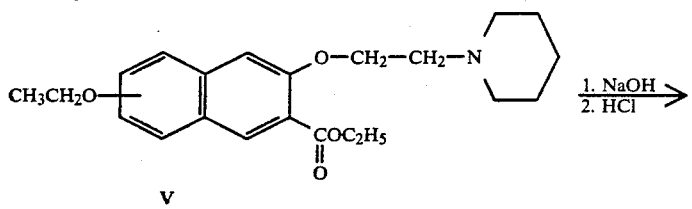

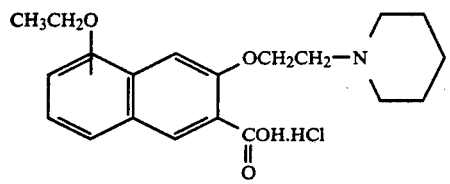

The dihydroxy acid, compound II, is obtained from a commercial source. The dihydroxy ester, compund III, is prepared by conversion of compound II to the corresponding acid chloride via thionyl chloride reaction with said acid, followed by esterfication of the acid chloride with ethanol. Compound III is then converted to the alkoxy-ester, compound IV, using an alkyl halide in the presence of sodium ethoxide in ethanol. The aminoether-ester, compound V, is obtained by treating compound IV with sodium ethoxide, followed by reacting the same with an aminoalkyl halide. Compound V then can be hydrolyzed, using a suitable base, such as sodium hydroxide, to obtain the desired dialkyloxy-acid, compound VI.

Representative examples for the preparation of illustrative compounds follow:

EXAMPLE 1

Ethyl 5-Benzyloxy-3-hydroxy-2-naphthoate

To a stirred solution of 7.8 g (0.34 g atom) of sodium in 1,000 cc of ethanol, was added 85 g (0.37 mole) of ethyl 3,5-dihydroxy-2-naphthoate. After one-half hour 47 g (0.37 mole) of benzyl chloride was added. The reaction mixture was warmed under reflux for 24 hours. The hot reaction mixture was filtered and cooled in an ice bath. A tan solid precipitated out, which was filtered off yielding 15.0 g (m.p. 98°–115° C.) of the crude product. Recrystallization first from ethanol and then from acetonitrile furnished ethyl 5-benzyloxy-3-hydroxy-2-naphthoate, m.p. 112°–114° C. in 7 percent yield (7.3 g).

EXAMPLE 2

Ethyl 5-Benzyloxy-3-(2-piperidinoethoxy)-2-naphthoate Hydrochloride

To a stirred solution of 1.4 g (0.062 g atom) of sodium, in 500 cc ethanol, was added 20 g (0.063 mole) of ethyl 5-benzyloxy-3-hydroxy-2-naphthoate. The reaction mixture was warmed to reflux for one hour. 2-Piperidinoethyl chloride (16.2 g 0.11 mole) dissolved in 100 cc of benzene was added dropwise to the reaction mixture. The benzene was removed by azeotropic distillation during which time the reaction volume was maintained at 500 cc by the periodic addition of ethanol. Refluxing was continued for 48 hours. The reaction mixture was filtered and the solvent removed from the filtrate. The residue was treated with water and extracted with ether. The ether solution was washed with water and then dried over anhydrous $MgSO_4$ Hydrogen chloride precipitated the hydrochloride salt which was then crystallized from acetonitrile to yield ethyl 5-benzyloxy-3-(2- piperidinoethoxy)-2-naphthoate hydrochloride, m.p. 163°–6° C. in 38 percent yield (10.8 g).

EXAMPLE 3

Ethyl 5-Hydroxy-3-(2-piperidinoethoxy)-2-naphthoate Hydrochloride

A solution of 8.8 g (0.019 mole) of ethyl 5-benzyloxy-3-(2-piperidinoethoxy)-2-naphthoate hydrochloride in 240 cc ethanol was treated with 1.0 g of 10 percent palladium on carbon and hydrogenated at room temperature. The reaction mixture was filtered and the solvent removed in vacuo. The residue, weighing 7.5 g on recrystallization from acetonitrile furnished ethyl 5-hydroxy-3-(2-piperidinoethoxy)-2-naphthoate-hydrochloride, m.p. 153°–6° C. in 61 percent yield (4.4 g).

In accordance with the procedures described in the above examples, the additional compounds shown in Table I below were prepared. In this table the melting points are for the hydrochloride salts.

TABLE I

| R  | $R_1$     | $R_2$           | n | m.p.°C. |
|----|-----------|-----------------|---|---------|
| Et | $Me_2N$   | $PhCH_2$        | 2 | 162–3   |
| Et | $Et_2N$   | $PhCH_2$        | 2 | 153–5   |
| Et | pyrrolidino | $PhCH_2$      | 2 | 179–80  |
| Et | $i-Pr_2N$ | $PhCH_2$        | 2 | 184–6   |
| Et | $Me_2N$   | $4-ClPhCH_2$    | 2 | 150–2   |
| Et | $Me_2N$   | $3,4-Cl_2PhCH_2$| 2 | 172–4   |
| Et | $Et_2N$   | $3,4-Cl_2PhCH_2$| 2 | 155–8   |
| Et | $Et_2N$   | $2,4-Cl_2PhCH_2$| 2 | 198–201 |
| Et | $Me_2N$   | $2,4-Cl_2PhCH_2$| 2 | 213–5   |
| Et | $Me_2N$   | $PhCH_2CH_2$    | 2 | 149–50  |
| Et | $Et_2N$   | $PhCH_2CH_2$    | 2 | 127–8   |
| Et | piperidino| $PhCH_2CH_2$    | 2 | 174–8   |
| Et | $i-Pr_2N$ | $PhCH_2CH_2$    | 2 | 149–51  |
| Et | $Me_2N$   | $PhCH_2CH_2CH_2$| 2 | 133–5   |
| Et | $Et_2N$   | $PhCH_2CH_2CH_2$| 2 | 128–9   |
| Et | piperidino| $PhCH_2CH_2CH_2$| 2 | 140–2   |
| Et | pyrrolidino | $PhCH_2CH_2CH_2$ | 2 | 126–30 |
| Et | $i-Pr_2N$ | $PhCH_2CH_2CH_2$| 2 | 155–7   |
| Et | $Me_2N$   | H               | 2 | 165–8   |

The compounds of the present invention inhibit the activity of 2,3-diphosphoglycerate phosphatase which then results in the maintenance and accumulation of 2,3-DPG levels in red blood cells. The increase of 2,3-DPG displaces in vitro the oxygen-dissociation curve to the right of normal in whole human blood. Thus, the compounds are useful to provide a more effective delivery of oxygen to the tissues of mammals under certain circumstances and conditions when tissue hypoxia occurs. The prior art is cognizant of such conditions which include anemia, trauma and shock, heart and lung diseases, diabetes, conditions associated with increased oxygen demand such as strenuous exercise, mountain climbing and the like, and certain surgical procedures.

The compounds may also be used in vitro both to maintain the oxygen delivery capacity of red blood cells and to extend shelf-life of transfusable blood on storage.

Form and Dosage of Administration

According to the invention, the disclosed compounds may be utilized for effective delivery of oxygen to tissues in a mammal. For administration to a recipient, one or more compounds are formulated in compositions such as tablets, capsules or elixirs for oral administration or in sterile solutions or suspensions for parenteral administration. About 28 to 56,000 mg of a compound or mixture of compounds above-disclosed or physiologically acceptable salts(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage is in the range of from 0.4 mg/kg to 800 mg/kg body weight of the patient per day, more preferably in the range of from 4.0 mg/kg to 400 mg/kg of body weight per day, and most preferably in the range of from 10 mg/kg to 160 mg/kg of body weight.

A single dose, or preferably two to four divided daily doses, provided on a basis of about 0.2 to 400 mg/kg per day, preferably about 2 to 200 mg/kg per day is appropriate. The substance is preferably administered orally, but a parenteral route such as subcutaneously, intramuscularly, intravenously or intraperitoneally can also be employed.

Illustrative of the adjuvenants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

When used for extracorporeal treatment and in vitro storage of red blood cells, an effective blood concentration of a compound according to the invention will generally be in the range of from 0.001 mM to 10 mM, more preferably in the range of from 0.01 mM to 5 mM, and most preferably from 0.025 mM to 2 mM.

The method of introducing a composition of the invention into the blood for extracorporeal treatment is analogous to the technique used in hemodialysis whereby blood is withdrawn from the patient, admixed with a composition and passed back to the patient. The blood, of course, may also be treated batch by batch as necessary prior to transfusion. For storage, the blood is admixed with the composition in the collection vessel and transferred to appropriate storage containers using sterile techniques and storage conditions employed in the art.

Method of Testing

2,3-Diphosphoglycerate Phosphatase Assay

The activity of 2,3-DPG phosphatase was determined radiochemically using a method based on Rose et al. (J. Biol. Chem. 245, 3232–3241, 1970). In this method the activity of the phosphatase is measured by determining the release of inorganic phosphate from the substrate, 2,3-DPG. The test compounds were dissolved in dimethyl sulfoxide at 100 times the final concentration used and then added to the reaction mixture at the beginning of the assay period. In the control experiments equivalent concentration of dimethyl sulfoxide was used.

14 $\mu$g of 2,3-DPG phosphatase was incubated in 0.2 ml of TES, at pH 7.5, containing 110 $\mu$M $^{32}$p-labeled 2,3-DPG (having a specific activity of 70 to 200 $\mu$Ci/$\mu$mol) 5 $\mu$M phosphoglycolate and 5 $\mu$M mercaptoethanol at 37° C. for 20 minutes in the presence and absence of the test compound. At the end of incubation the reaction was stopped by the addition of 0.1 ml of 15% w/v trichloroacetic acid and the sample was centrifuged (Eppendorf microfuge, Model 5413) in order to remove protein precipitates. Then 0.2 ml of the supernatant was withdrawn and mixed with 0.1 ml of 8 M sulfuric acid, 0.1 ml of 5% w/v ammonium molybdate and 0.6 ml of water. The mixture then was extracted with 2 ml of isobutanol/benzene (1:1,v/v) and then centrifuged to effect separation of the phases. 1 ml of the organic phase containing the extracted $^{32}$p-phosphate was counted in a scintillation counter (Beckman, Model LS 8,000) using a program for $^{32}$p-radioactivity. The activity of the enzyme was expressed as number of mole phosphate release per minute.

From the data obtained by employing the test method above-described, the percent inhibition of 2,3-DPG phosphatase was calculated and is shown in Table II.

TABLE II

| Compound(100 $\mu$M) | % Inhibition |
|---|---|
| a | 79.2 |
| b | 94.3 |
| c | 94.3 |
| d | 92.5 |
| g | 89.6 |
| h | 74.0 |
| p | 99.2 |
| q | 97.7 |
| r | 97.1 |
| s | 95.6 |
| t | 94.2 |
| u | 86.9 |
| v | 89.0 |
| w | 93.6 |
| x | 100.0 |

TABLE II-continued

| Compound(100 μM) | % Inhibition |
| --- | --- |
| y | 81.9 |

While the invention in a method to enhance oxygen availability to mammalian tissue and to maintain and increase of 2,3-DPG levels in red blood cells has been described in detail, it will be recognized by those skilled in the art that considerable variation can be made in such detail without departing from the spirit of the invention as claimed.

What is claimed is:

1. A method of maintaining oxygen-delivery capacity of transfusable blood cells comprising admixing said blood prior to transfusion with an effective amount of a compound of the formula

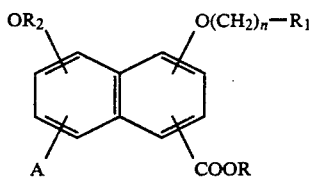

wherein
R is H, alkyl, aryl or aminoalkyl;
$R_1$ is $NR_3R_4$ where $R_3$ and $R_4$ form a cyclic amino group with N to which they are attached;
$R_2$ is H, acyl, aminoacyl, alkyl, substituted alkyl wherein the substituents are aryl, cycloalkyl, azacycloalkyl, CONHR, aryloxy or alkoxyalkyl;
A is H, halo, $CF_3$, OH,

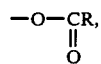

aminoalkyl, aryl, acyl, alkoxy, alkyloxy, or alkoxyalkyloxy; and
n is 0–6; wherein said alkyl group in alkyl, aminoalkyl, substituted alkyl, alkoxyalkyl, and alkoxyalkyloxy contains up to 8 carbon atoms and said cycloalkyl group contains 3 to 10 carbon atoms or pharmaceutically acceptable salts thereof.

2. The method of claim 1 wherein said kausfusable blood cell cells are human blood cells.

3. A method of extending the shelf-life of transfusable red blood cells comprising: admixing said red blood cells with a compound of the formula

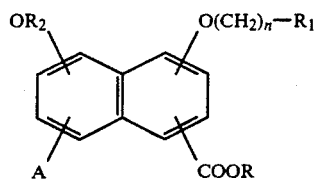

wherein
R is H, alkyl, aryl or aminoalkyl;
$R_1$ is $NR_3R_4$ where $R_3$ and $R_4$ form a cyclic amino group with N to which they are attached;
$R_2$ is H, acyl, aminoacyl, alkyl, substituted alkyl wherein the substituents are aryl, cycloalkyl, azacycloalkyl, COHNR, aryloxy or alkoxyalkyl;
A is H, halo, $CF_3$, OH,

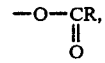

aminoalkyl, aryl, acyl, alkoxy, alkyloxy, or alkoxyalkyloxy; and
n is 0–6; wherein said alkyl group in alkyl, aminoalkyl, substituted alkyl, alkoxyalkyl, and alkoxyalkyloxy contains up to 8 carbon atoms and said cycloalkyl group contains 3 to 10 carbon atoms or pharmaceutically acceptable salts thereof; and storing the same under physiologically acceptable conditions prior to transfusion.

4. The method of claim 3 wherein said compound is ethyl 5-benzyloxy-3-(2-piperidinoethoxy)-2-naphthoate.

5. The method of claim 3 wherein said compound is ethyl 5-hydroxy-3-(2-piperidinoethoxy)-2-naphthoate.

6. The method of claim 3 wherein said compound is ethyl 5-cyclohexylmethoxy-3-(2-(1-azacycloheptyl)ethoxy-2-naphthoate.

7. The method of claim 3 wherein said compound is ethyl 5-(3-phenylpropoxy)-3-(2-piperidinoethoxy)-2-naphthoate.

8. The method of claim 3 wherein said compound is 3,5-bis[2(1-pyrrolidinyl)ethoxy]-2-naphthoate.

* * * * *